(12) United States Patent
Adler et al.

(10) Patent No.: US 8,563,345 B2
(45) Date of Patent: *Oct. 22, 2013

(54) INTEGRATION OF STRUCTURALLY-STABLE ISOLATED CAPACITIVE MICROMACHINED ULTRASONIC TRANSDUCER (CMUT) ARRAY CELLS AND ARRAY ELEMENTS

(75) Inventors: Steven J. Adler, Saratoga, CA (US); Peter Johnson, Sunnyvale, CA (US); Gokhan Percin, Los Gatos, CA (US); Shahram Mostafazadeh, San Jose, CA (US)

(73) Assignee: National Semiconductor Corporated, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/419,216

(22) Filed: Mar. 13, 2012

(65) Prior Publication Data
US 2012/0187508 A1    Jul. 26, 2012

Related U.S. Application Data

(63) Continuation-in-part of application No. 12/587,139, filed on Oct. 2, 2009, now Pat. No. 8,222,065, and a continuation-in-part of application No. 12/589,754, filed on Oct. 28, 2009, now Pat. No. 8,324,006.

(51) Int. Cl.
*H01L 29/72* (2006.01)
(52) U.S. Cl.
USPC ............... 438/50; 438/48; 257/416; 310/322; 600/437
(58) Field of Classification Search
USPC ........ 438/48, 50; 257/416; 310/322; 600/437
See application file for complete search history.

(56) References Cited

U.S. PATENT DOCUMENTS

| 7,564,172 B1 | 7/2009 | Huang |
| 7,612,635 B2 | 11/2009 | Huang |
| 7,741,686 B2 | 6/2010 | Khuri-Yakub et al. |
| 7,759,839 B2 | 7/2010 | Huang |

(Continued)

OTHER PUBLICATIONS

Xuefeng Zhuang, et al., "Wafer-Bonded 2-D CMUT Arrays Incorporating Through-Wafer Trench-Isolated Interconnects with a Supporting Frame", IEEE Transactions on Ultrasonics, Ferroelectrics and Frequency Control, vol. 56, No. 1, Jan. 2009, p. 182-192.

(Continued)

*Primary Examiner* — Edward Wojciechowicz
(74) *Attorney, Agent, or Firm* — Eugene Conser; W. James Brady; Frederick J. Telecky, Jr.

(57) ABSTRACT

A method for forming a capacitive micromachined ultrasonic transducer (CMUT) includes forming multiple CMUT elements in a first semiconductor-on-insulator (SOI) structure. Each CMUT element includes multiple CMUT cells. The first SOI structure includes a first handle wafer, a first buried layer, and a first active layer. The method also includes forming a membrane over the CMUT elements and forming electrical contacts through the first handle wafer and the first buried layer. The electrical contacts are in electrical connection with the CMUT elements. The membrane could be formed by bonding a second SOI structure to the first SOI structure, where the second SOI structure includes a second handle wafer, a second buried layer, and a second active layer. The second handle wafer and the second buried layer can be removed, and the membrane includes the second active layer.

15 Claims, 7 Drawing Sheets

(56) References Cited

U.S. PATENT DOCUMENTS

| | | | |
|---|---|---|---|
| 7,846,102 B2 | 12/2010 | Kupnik et al. | |
| 7,880,565 B2 | 2/2011 | Huang | |
| 8,008,105 B2 | 8/2011 | Huang | |
| 8,018,301 B2 | 9/2011 | Huang | |
| 8,324,006 B1 * | 12/2012 | Adler et al. | 438/50 |
| 2006/0075818 A1 | 4/2006 | Huang et al. | |
| 2006/0238067 A1 | 10/2006 | Dausch | |
| 2007/0122074 A1 | 5/2007 | Kim et al. | |
| 2007/0228878 A1 | 10/2007 | Huang | |
| 2007/0264732 A1 | 11/2007 | Chen | |
| 2008/0048211 A1 | 2/2008 | Khuri-Yakub et al. | |
| 2008/0194053 A1 | 8/2008 | Huang | |
| 2008/0197751 A1 | 8/2008 | Huang | |
| 2008/0203556 A1 | 8/2008 | Huang | |
| 2008/0290756 A1 | 11/2008 | Huang | |
| 2009/0140606 A1 | 6/2009 | Huang | |
| 2009/0148967 A1 | 6/2009 | Wodnicki et al. | |
| 2009/0152980 A1 | 6/2009 | Huang | |
| 2009/0250729 A1 | 10/2009 | Lemmerhirt et al. | |
| 2010/0013574 A1 | 1/2010 | Huang | |
| 2010/0255623 A1 | 10/2010 | Huang | |
| 2010/0280388 A1 | 11/2010 | Huang | |
| 2011/0040189 A1 | 2/2011 | Petruzzello et al. | |
| 2011/0073968 A1 | 3/2011 | Ezaki et al. | |
| 2011/0136284 A1 | 6/2011 | Huang | |
| 2011/0215677 A1 | 9/2011 | Jiang et al. | |
| 2011/0254109 A1 | 10/2011 | Ossmann et al. | |

OTHER PUBLICATIONS

Y. Huang, et al., "Fabricating Capacitive Micromachined Ultrasonic Transducers with Wafer-Bonding Technology", 5 pages.

K. K. Park, et al., "Fabricating Capacitive Micromachined Ultrasonic Transducers with Direct Wafer-Bonding and Locos Technology", MEMS 2008, Tucson, AZ, USA, Jan. 13-17, 2008, p. 339-342.

Steven J. Adler, et al., "Method of Forming a Capacitive Micromachined Ultrasonic Transducer (CMUT) and Related Apparatus", U.S. Appl. No. 12/589,754, filed Oct. 28, 2009.

* cited by examiner

INTEGRATION OF STRUCTURALLY-STABLE ISOLATED CAPACITIVE MICROMACHINED ULTRASONIC TRANSDUCER (CMUT) ARRAY CELLS AND ARRAY ELEMENTS

CROSS-REFERENCE TO RELATED APPLICATIONS AND PRIORITY CLAIM

This application claims priority under 35 U.S.C. §120 as a continuation-in-part to the following U.S. patent applications:

U.S. patent application Ser. No. 12/587,139 filed on Oct. 2, 2009 now U.S. Pat. No. 8,222,065 and entitled "METHOD AND SYSTEM FOR FORMING A CAPACITIVE MICROMACHINED ULTRASONIC TRANSDUCER"; and U.S. patent application Ser. No. 12/589,754 filed on Oct. 28, 2009 now U.S. Pat. No. 8,324,006 and entitled "METHOD OF FORMING A CAPACITIVE MICRO-MACHINED ULTRASONIC TRANSDUCER (CMUT) AND RELATED APPARATUS". Both of these applications are hereby incorporated by reference.

TECHNICAL FIELD

This disclosure is generally directed to integrated circuit fabrication. More specifically, this disclosure is directed to the integration of structurally-stable isolated capacitive micromachined ultrasonic transducer (CMUT) array cells and array elements.

BACKGROUND

Capacitive micromachined ultrasonic transducer (CMUT) devices typically include membranes capacitively coupled to underlying structures. CMUT devices have been used increasingly in medical imaging applications. For example, CMUT devices have been able to improve medical ultrasound imaging probes and to provide high-intensity focused ultrasound for use in medical therapy.

One manufacturing technique for CMUT devices uses a standard micro-electro-mechanical system (MEMS) fabrication method in which a release layer is etched out from under a layer of material, leaving a free-standing membrane. An alternative manufacturing technique involves bonding a silicon-on-insulator wafer to another structure, where removal of a handle wafer and a buried oxide layer leaves a single-crystal silicon membrane on the underlying structure.

In a typical CMUT device, individual capacitor cells are grouped into elements, and multiple elements are combined to form an array (such as a one-dimensional or two-dimensional array). One integration challenge with a CMUT array, particularly a two-dimensional array, is making electrical contact with individual cells or elements without introducing excessive parasitic capacitance and without etching a series of isolation trenches that excessively weaken the array structurally.

BRIEF DESCRIPTION OF THE DRAWINGS

For a more complete understanding of this disclosure and its features, reference is now made to the following description, taken in conjunction with the accompanying drawings, in which.

DETAILED DESCRIPTION

FIGS. 1 through 5, discussed below, and the various embodiments used to describe the principles of the present invention in this patent document are by way of illustration only and should not be construed in any way to limit the scope of the invention. Those skilled in the art will understand that the principles of the present invention may be implemented in any suitable manner and in any type of suitably arranged device or system.

Figure 1A:
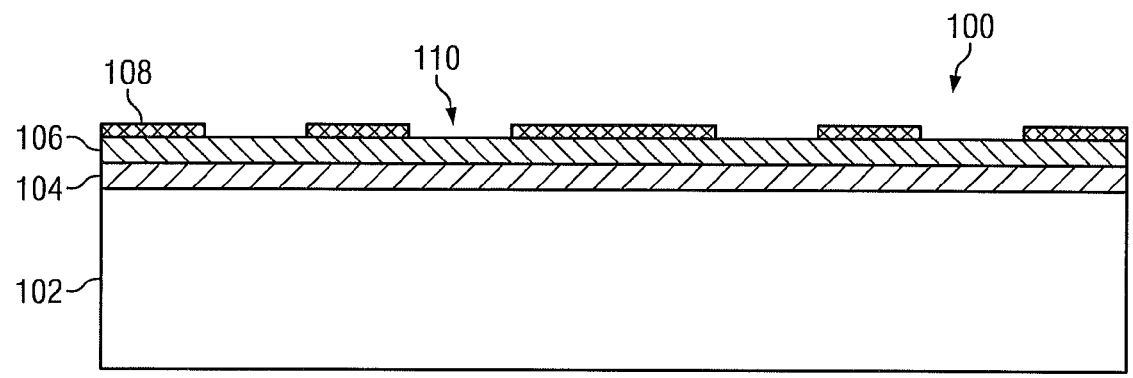
FIGS. 1A through 1H illustrate example fabrication steps for integrating structurally-stable isolated capacitive micromachined ultrasonic transducer (CMUT) array cells and array elements in accordance with this disclosure.

FIGS. 1A through 1H illustrate example fabrication steps for integrating structurally-stable isolated capacitive micromachined ultrasonic transducer (CMUT) array cells and array elements in accordance with this disclosure. As shown in FIG. 1A, a semiconductor-on-insulator (SOI) structure 100 includes a handle wafer 102, a buried layer 104, and an active layer 106. The handle wafer 102 represents any suitable semiconductor wafer formed from any suitable material(s), such as undoped or lightly-doped silicon. The buried layer 104 represents any suitable layer(s) of insulative material(s), such as an oxide layer. The active layer 106 represents any suitable layer(s) of material(s) in which integrated circuit devices can be formed, such as heavily-doped silicon. In particular embodiments, the handle wafer 102 represents a silicon wafer that is more than 200 µm thick with high resistivity, the buried layer 104 represents an oxide layer that is about 2 µm thick, and the active layer 106 represents a heavily-doped silicon layer that is about 10 µm thick.

A first mask can be formed on the active layer 106, and front side alignment marks can be etched into the SOI structure 100. An oxide layer 108 can also be formed on the SOI structure 100. The oxide layer 108 could have any suitable thickness, such as about 0.6 µm. The oxide layer 108 could also be formed in any suitable manner. For example, the oxide layer 108 can be thermally grown on the SOI structure 100 by converting a portion of the active layer 106 into thermal oxide. A second mask can be formed over the oxide layer 108, and openings 110 can be etched through the oxide layer 108. The openings 110 define areas where CMUT cells are to be formed. The openings 110 can be formed in any suitable manner, such as by using a wet etch. The openings 110 can also have any suitable shape and size, such as about 36 µm in diameter.

Figure 1B:
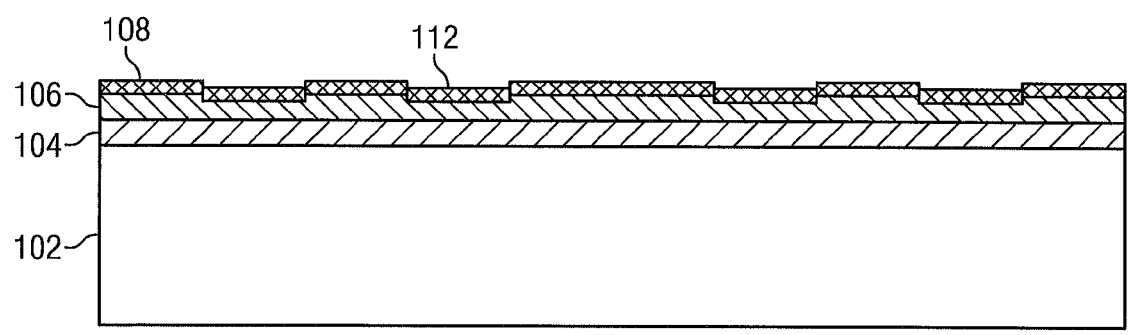

As shown in FIG. 1B, an oxidation process occurs that increases the thickness of the remaining portions of the oxide layer 108 and forms oxide regions 112 in the active layer 106 under the openings 110. Any suitable oxidation process could be used here, such as a thermal oxidation process. Also, the oxide regions 112 could have any suitable thickness, such as about 0.3 µm (where the oxidation process consumes about 0.15 µm of silicon in the active layer 106).

Figure 1C:
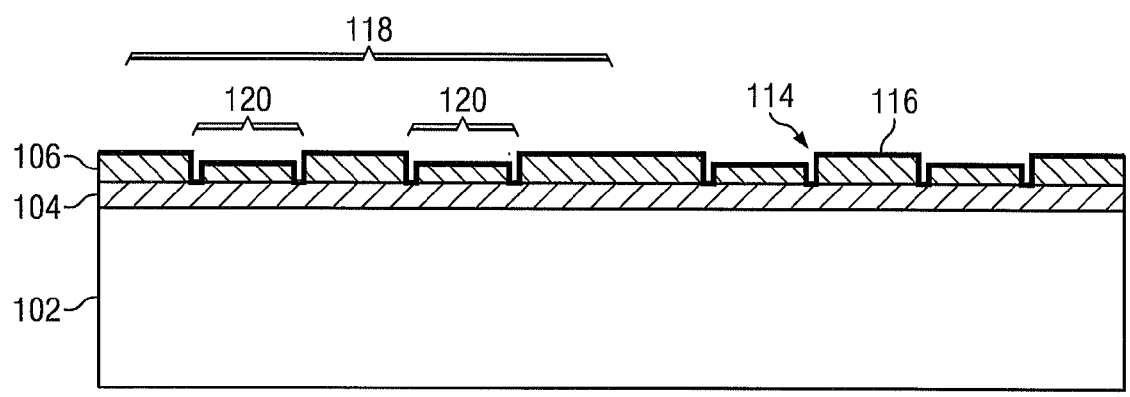

As shown in FIG. 1C, the remaining portions of the oxide layer 108 and the oxide regions 112 are removed. This could be done, for example, using a wet strip. The resulting structure has recesses in the active layer 106 where the oxide regions 112 were formed. The active layer 106 in those recessed areas is thinner, such as by about 0.14 μm. The actual depth of the recesses can be well controlled by the thermal oxidation process that is used to form the oxide regions 112.

A third mask can be formed over the active layer 106, and multiple isolation trenches 114 can be formed through the active layer 106 down to the buried layer 104. The trenches 114 can be formed in any suitable manner, such as by using a plasma etch process. Note that Upper surfaces of the active layer 106 can remain substantially undamaged during these steps, since surfaces with little or no damage can help provide more robust wafer bonding (described below). In this example, the isolation trenches 114 can be formed around each CMUT cell being fabricated. An oxide layer 116 is then formed over the structure. The oxide layer 116 could be formed in any suitable manner, such as by using a thermal oxidation process. Also, the oxide layer 116 could have any suitable thickness, such as about 0.3 μm.

In this example, the process is used to form multiple CMUT elements 118, each of which includes multiple CMUT cells 120. Note that while each CMUT element 118 here includes two CMUT cells 120, a CMUT element 118 could include any number of CMUT cells 120 (such as twenty-five cells). Also note that after formation of the oxide layer 116, the resulting structure could be very flat to support wafer bonding.

Figure 1D:
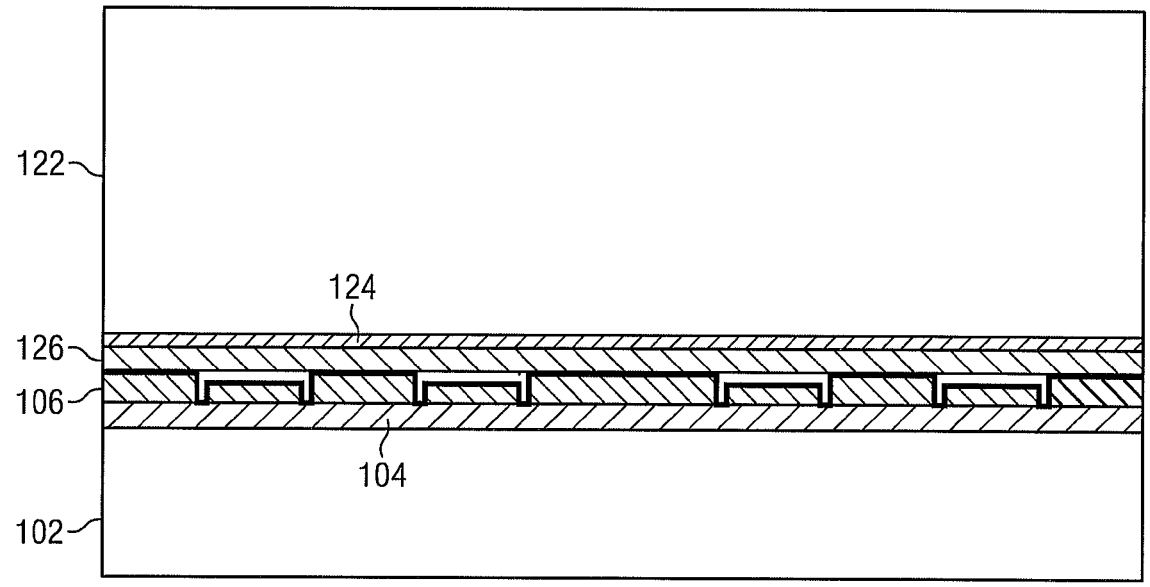

As shown in FIG. 1D, another wafer is bonded to the structure. The second wafer in this example is another SOI structure that includes a handle wafer 122, a buried layer 124, and an active layer 126. The handle wafer 122 represents any suitable semiconductor wafer formed from any suitable material(s), such as undoped or lightly-doped silicon. The buried layer 124 represents any suitable layer(s) of insulative material(s), such as an oxide layer. The active layer 126 represents any suitable layer(s) of material(s) suitable for use as a membrane in a CMUT device. The active layer 126 could, for instance, represent a single-crystal silicon layer having any suitable thickness, such as about 1.2 μm. The active layer of a SOI structure can be formed in any suitable manner, such as by bonding a silicon wafer to a handle wafer with an oxide layer in between and then thinning and polishing the silicon wafer to a desired thickness.

Any suitable technique could be used to bond the wafers together, such as vacuum fusion bonding. Note that the time between formation of the oxide layer 116 and wafer bonding could be minimized. Various pre-bonding treatments like plasma activation or deionized water rinse could also used to enhance the bond strength. By bonding the wafers in this manner, the CMUT cells 120 are protected against further contamination, and the active layer 126 becomes the grounded top plate of the CMUT cells 120.

The thickness of the handle wafer 102 in FIG. 1D can also be reduced to a desired thickness, such as about 200 μm. This can be accomplished in any suitable manner, such as by performing a back grind and polish. In addition, a fourth mask can be used to etch backside alignment marks into the handle wafer 102.

Figure 1E:
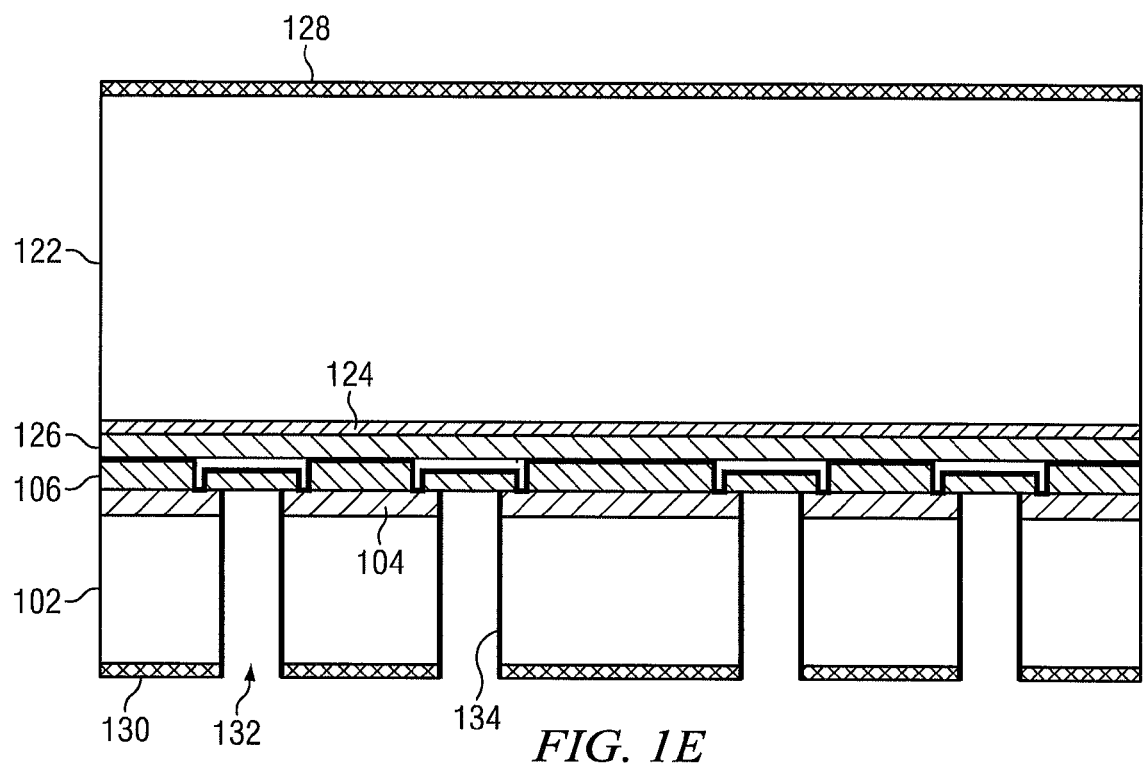

As shown in FIG. 1E, nitride layers 128-130 are formed on the top and bottom surfaces of the bonded structures. The nitride layers 128-130 could be formed in any suitable manner, such as by using low-pressure chemical vapor deposition (LPCVP). Also, each of the nitride layers 128-130 could have any suitable thickness, such as about 0.5 μm.

A fifth mask can be formed and used to etch vias 132 through the backside of the bonded structures. This etch etches through the nitride layer 130, the handle wafer 102, and the buried layer 104 and stops at the active layer 106 (note that some over-etching may occur). In this example, one via 132 is formed to each CMUT cell 120 in each CMUT element 118. The vias 132 could be formed in any suitable manner. Also, the vias 132 could have any suitable size and shape. In particular embodiments, each of the vias 132 has a diameter of about 20 μm and an aspect ratio of about 10:1.

In addition, an oxide layer 134 is formed over the backside of the bonded structures and within the vias 132, and a spacer etch is used to remove the oxide layer 134 from the active layer 106 without etching the nitride layer 130. The oxide layer 134 could be formed in any suitable manner, such as thermal oxidation. The oxide layer 134 could also have any suitable thickness, such as about 0.5 μm.

Note that in FIG. 1E, backside trenches are not needed to isolate the different CMUT elements 118. As a result, the overall structure is stronger, allowing the handle wafer 102 to be thinned below 200 μm with little or no danger of breaking. Among other things, a thinner handle wafer 102 can make a subsequent "via fill" operation easier to accomplish.

Figure 1F:
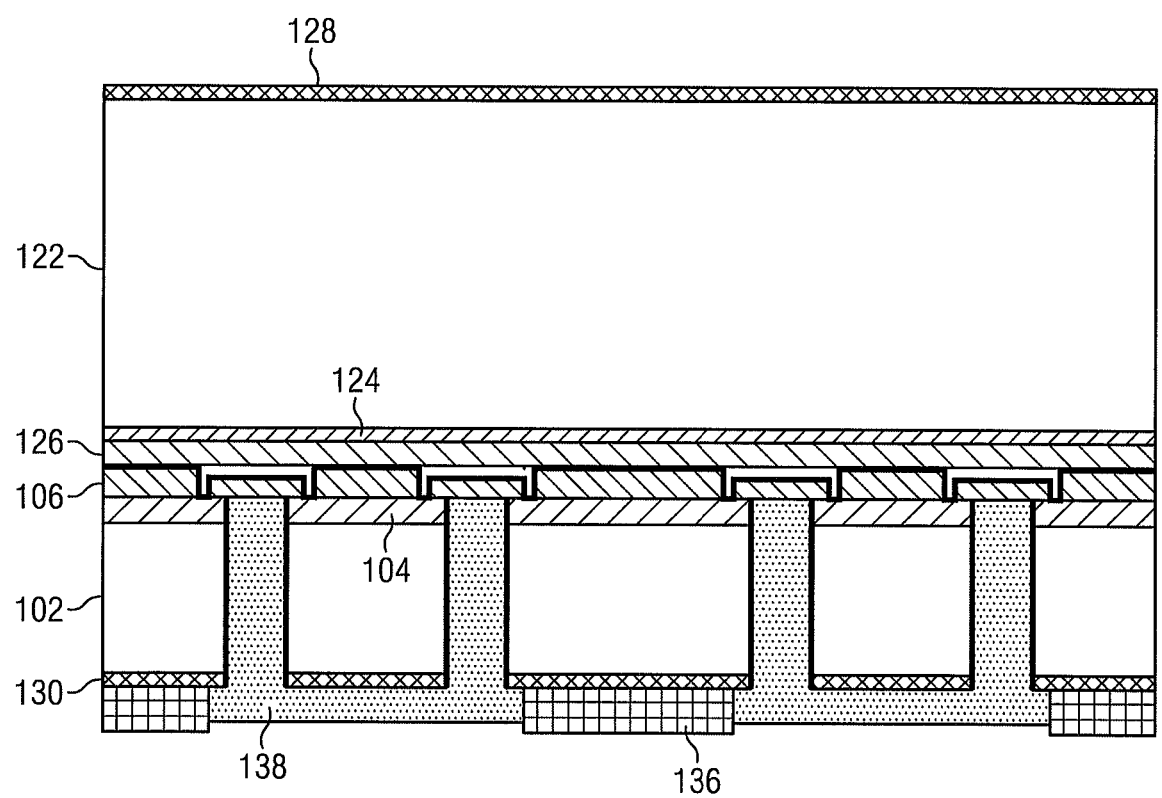
Figure 1G:
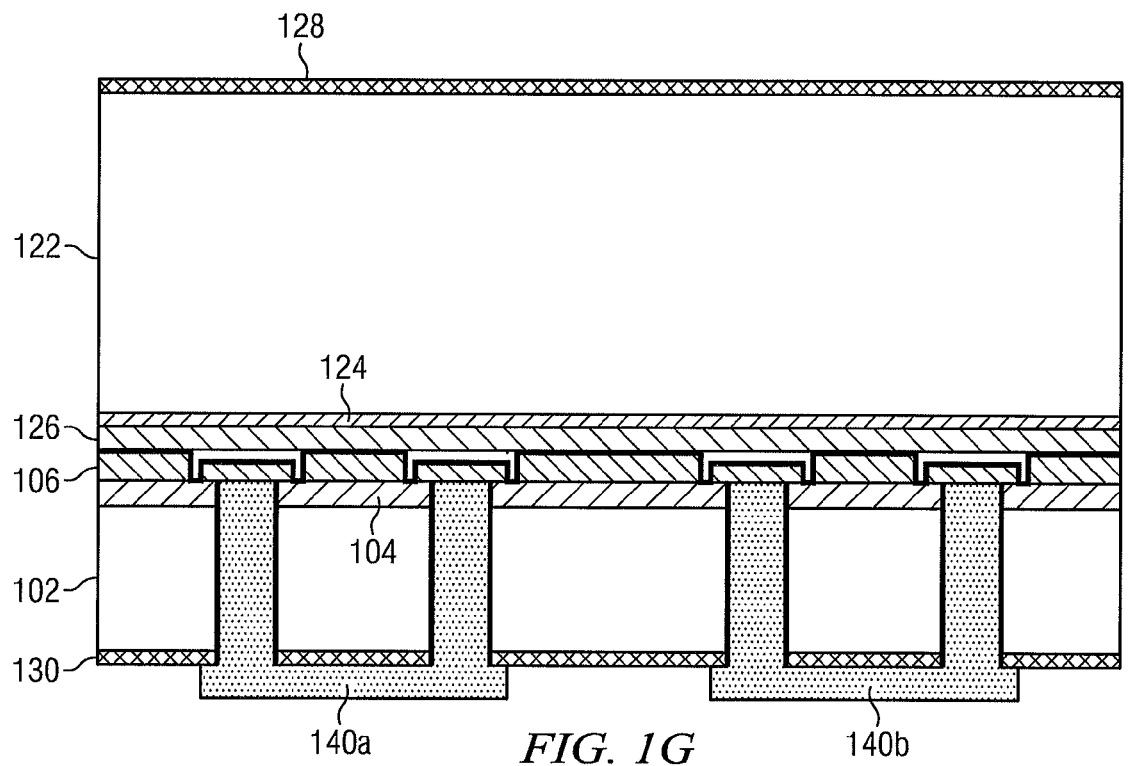

As shown in FIG. 1F, a sixth mask 136 (a mold mask) is formed over the backside of the bonded structures, and conductive material 138 is deposited in the vias 132 and over parts of the backside. In some embodiments, a titanium and copper seed layer can be formed over the backside of the bonded structures, the mask 136 can be formed over the seed layer, and copper can be electroplated onto the exposed portions of the seed layer to fill the vias 132 and electrically couple adjacent filled vias. The mask 136 is removed as shown in FIG. 1G, leaving two electrical contacts 140a-140b to multiple cells 120 of two CMUT elements 118. Note that the use of electroplated copper is for illustration only, and any other suitable conductive material(s) 138 could be used. For instance, polysilicon or other conductive material could be deposited in the vias 132 and over the backside of the bonded structures and then etched to form the electrical contacts 140a-140b.

Figure 1H:
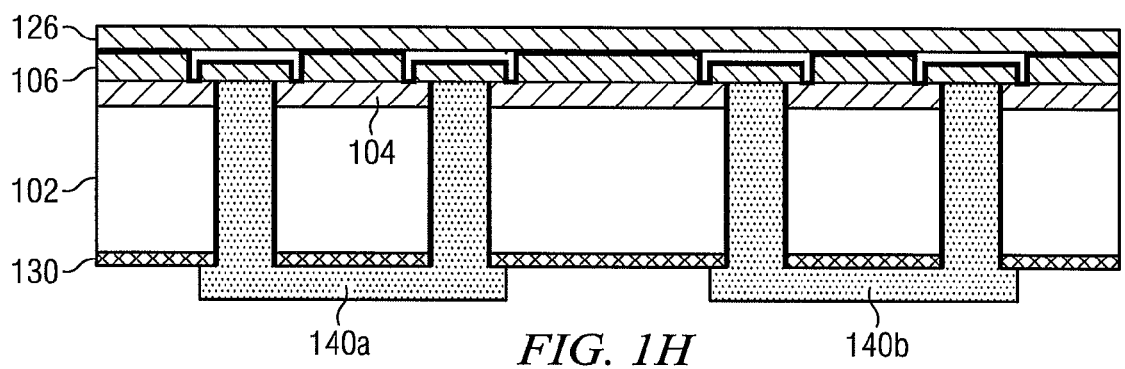

As shown in FIG. 1H, the top SOI structure is processed to remove the nitride layer 128, the handle wafer 122, and the buried layer 124. For example, the handle wafer 122 could be ground or cut, and the buried layer 124 could be stripped. The remaining active layer 126 is a membrane forming the top electrode of various CMUT cells 120 and can be contacted around the edge of the CMUT array. Although not shown, if the resistance of the active layer 126 is too high, it could be strapped with a metal or silicide layer or in any other suitable manner.

At this point, multiple CMUT cells 120 have been formed in multiple CMUT elements 118, which can be arranged in an array. Electrical contacts (including contacts 140a-140b) can be used to electrically couple the array to an external device or system, such as processing circuitry configured to process signals generated by the array. Note that since FIGS. 1A through 1H are cross-sections of a CMUT array, the CMUT elements 118 appear linear in a one-dimensional array. However, a CMUT array could include any number of CMUT elements 118 in any suitable one-dimensional or multi-dimensional array, and each CMUT element 118 could include any number of CMUT cells 120.

Although FIGS. 1A through 1H illustrate one example of fabrication steps for integrating structurally-stable isolated CMUT array cells and array elements, various changes may be made to FIGS. 1A through 1H. For example, each structure shown in FIGS. 1A through 1H could be formed from any suitable material(s) and in any suitable manner. The techniques described above for forming the various structures are for illustration only, and other techniques could be used to form the same or similar structures. Also, FIGS. 1A through 1H are not drawn to scale, and each structure shown in FIGS. 1A through 1H could have any suitable size, shape, and dimensions. Individual CMUT elements/cells and their membranes could, for instance, have circular, square, rectangular, hexagonal, or honey-comb shapes.

Figure 2:
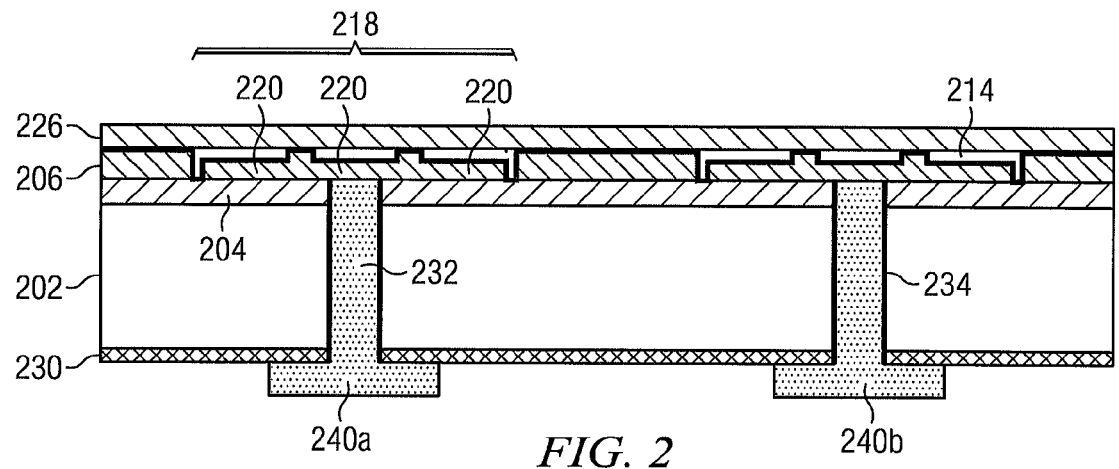
FIGS. 2 and 3 illustrate alternate fabrication steps for integrating structurally-stable isolated CMUT array cells and array elements in accordance with this disclosure.
Figure 3:
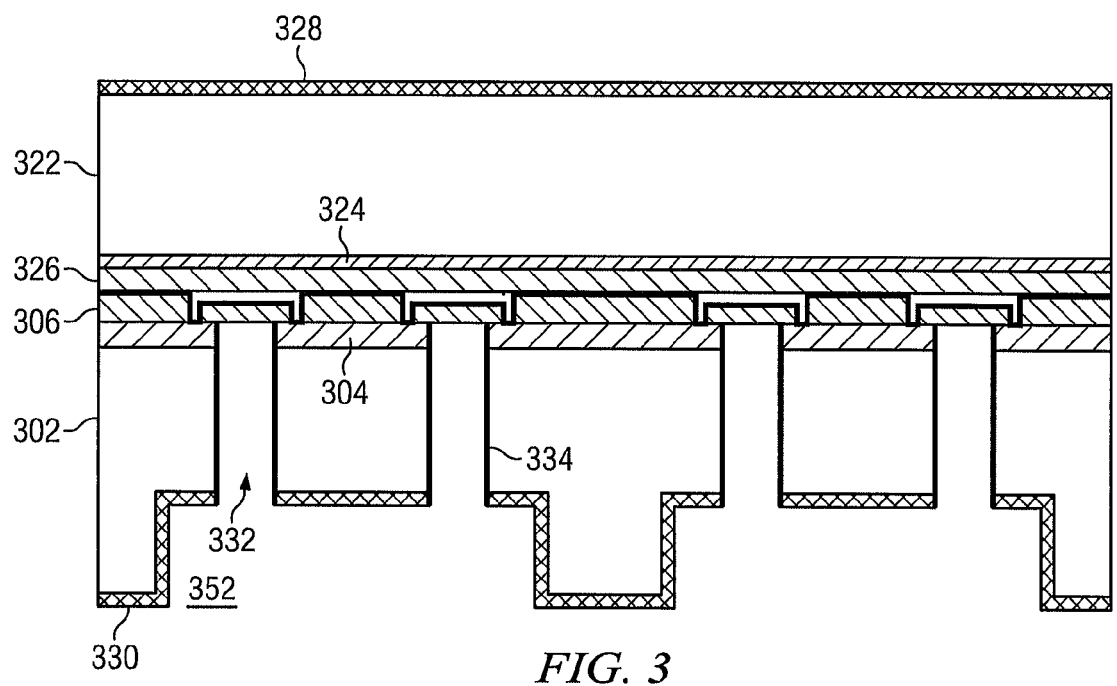

FIGS. 2 and 3 illustrate alternate fabrication steps for integrating structurally-stable isolated CMUT array cells and array elements in accordance with this disclosure. The fabrication steps shown in FIGS. 2 and 3 could, for example, be used in place of corresponding fabrication steps shown in FIGS. 1A through 1H.

As shown in FIG. 2, a single filled via could be used with each CMUT element, rather than with each CMUT cell. In FIG. 2, a first SOI structure includes a handle wafer 202, a buried layer 204, and an active layer 206. However, the active layer 206 has been patterned differently than in FIGS. 1A through 1H. Namely, multiple CMUT cells 220 in a CMUT element 218 are formed by a continuous portion of the active layer 206, and isolation trenches 214 are etched around the edge of each CMUT element 218 but not around each CMUT cell 220. In FIG. 2, there are two three-cell CMUT elements 218 shown, although any number of CMUT elements 218 could be used, and each CMUT element 218 could include any number of CMUT cells 220.

An active layer 226 represents the remaining portion of a second SOI structure that was bonded to the first SOI structure and then processed as described above. A nitride layer 230, the handle wafer 202, and the buried layer 204 are etched to form a single via 232 for each CMUT element 218. The sides of the vias 232 are covered by an oxide layer 234, and the vias 232 are filled with conductive material to form electrical contacts 240a-240b.

In the structure of FIG. 2, a smaller number of filled vias are used compared to FIGS. 1A through 1H. This increases the strength of the handle wafer 202 and reduces the parasitic capacitance in the overall structure compared to the structure formed in FIGS. 1A through 1H.

The structure shown in FIG. 2 could be fabricated in a manner similar to that shown in FIGS. 1A through 1H. However, the processing steps shown in FIGS. 1A through 1C would be modified to form the CMUT elements 218 and cells 220 shown in FIG. 2. Also, the via formation and filling steps shown in FIGS. 1E through 1G would be modified to form fewer filled vias as shown in FIG. 2.

In FIG. 3, a different technique is shown for forming vias to CMUT elements or CMUT cells. As shown in FIG. 3, a first SOI structure includes a handle wafer 302, a buried layer 304, and an active layer 306. A second SOI structure includes a handle wafer 322, a buried layer 324, and an active layer 326. A nitride layer 328 is formed over the handle wafer 322.

In FIG. 3, the handle wafer 302 can be thicker and need not have its thickness reduced as is done in FIG. 1D. Instead, vias 332 through the handle wafer 302 and the buried layer 304 are formed within recesses 352. The recesses 352 represent larger openings in the handle wafer 302, and one or multiple vias 332 could be formed in each recess 352. Also, the larger portions of the electrical contacts could be formed within the recesses 352. The presence of conductive material filling the recesses 352 can provide additional strength to the overall structure.

The recesses 352 could be formed in any suitable manner. For example, the recesses 352 can be formed using an additional mask before deposition of a nitride layer 330. Also, the recesses 352 could have any suitable size and shape. In particular embodiments, the handle wafer 302 is about 400 μm thick, and the recesses 352 are about 200 μm deep (so that the vias 332 remain about 200 μm in height).

The structure shown in FIG. 3 could be fabricated in a manner similar to that shown in FIGS. 1A through 1H. However, thinning of the handle wafer may not be needed in FIG. 1D, the step shown in FIG. 1E would be modified to form recesses and vias, and the steps shown in FIGS. 1F through 1H would be used to fill the vias 332 and recesses 352 and to process the upper SOI structure.

Although FIGS. 2 and 3 illustrate examples of alternate fabrication steps for integrating structurally-stable isolated CMUT array cells and array elements, various changes may be made to FIGS. 2 and 3. For example, the single via per CMUT element as shown in FIG. 2 could be recessed as shown in FIG. 3. Also, note that a combination of approaches could be used, such as when single vias are used for some CMUT elements and single vias are used for CMUT cells in other CMUT elements.

Figure 4:
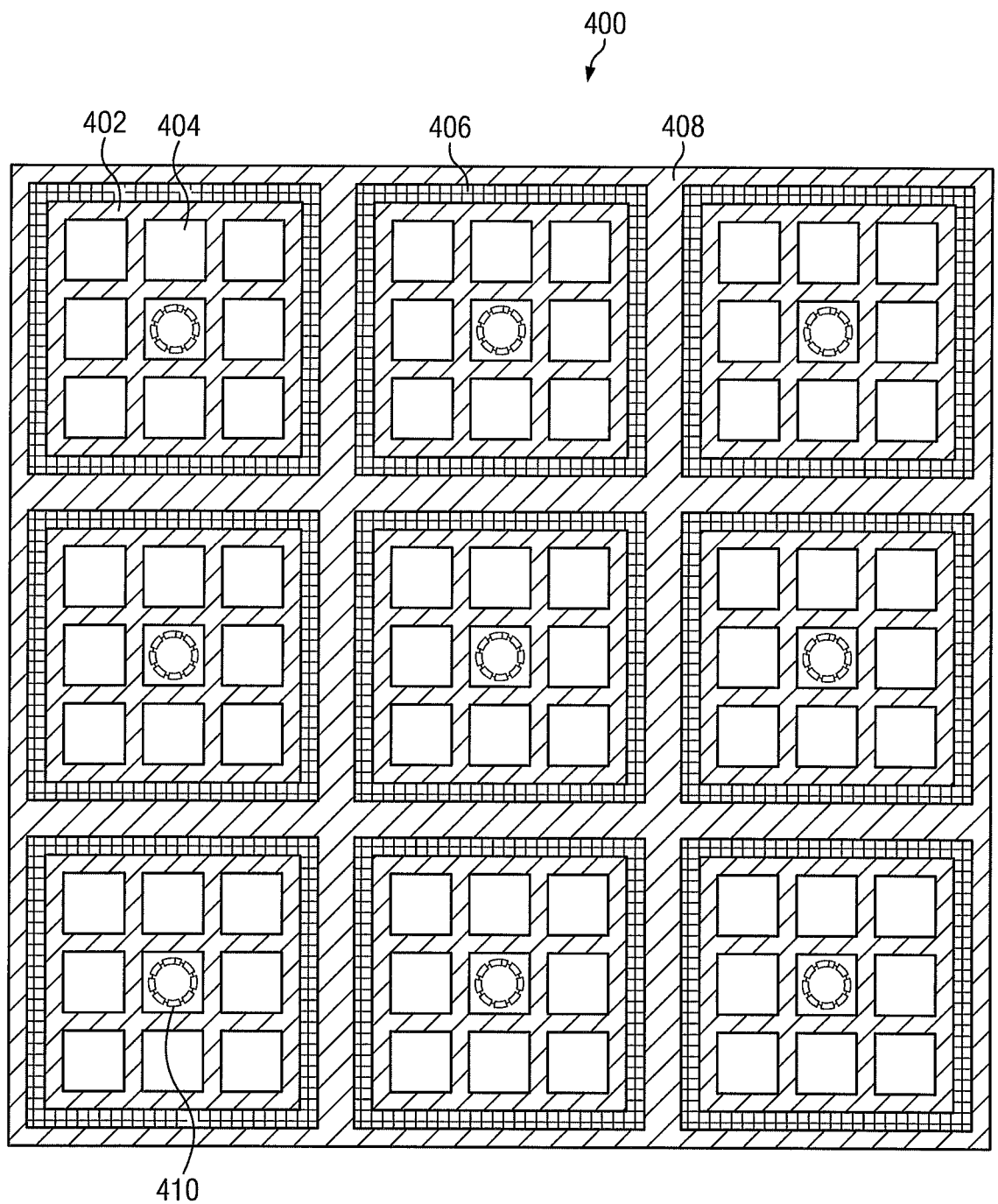
FIG. 4 illustrates a top view of an example CMUT array having integrated structurally-stable isolated CMUT array cells and array elements in accordance with this disclosure.

FIG. 4 illustrates a top view of an example CMUT array 400 having integrated structurally-stable isolated CMUT array cells and array elements in accordance with this disclosure. As shown in FIG. 4, the array 400 includes a three-by-three array of CMUT elements 402. Each CMUT element 402 includes a three-by-three array of CMUT cells 404.

An isolation trench 406 is formed around the CMUT cells 404 in each CMUT element 402, which helps to electrically isolate the CMUT element 402. These isolation trenches 406 could, for example, extend down to a buried oxide layer in an underlying SOI structure (where the CMUT cells 404 are formed over the buried layer). The isolation trenches 406 could be formed in any suitable manner and filled with any suitable material(s), such as an oxide.

A post oxide 408 can cover or separate various other elements of the CMUT array 400. For example, the post oxide 408 could cover or separate the CMUT cells 404 in each CMUT element 402, and the post oxide 408 could cover or separate the CMUT elements 402. The post oxide 408 includes any suitable oxide material(s).

Vias 410 are electrically connected to the CMUT elements 402 through the backside of the array 400. Since FIG. 4 shows a top view of the array 400, the vias 410 are shown in dashed lines to illustrate that they are formed on the opposite side of the structure. In this example, a via 410 is formed for each CMUT element 402.

While not specifically shown, a membrane can be formed over the CMUT elements 402 in FIG. 4. For example, a transparent silicon or other plate can be formed over the CMUT elements 402, such as by bonding the CMUT elements 402 to an SOI structure and then removing the handle wafer and buried layer of the SOI structure. Note that a single membrane could cover all CMUT elements 402 in FIG. 4, or multiple membranes (such as membranes covering one CMUT element or a subset of the CMUT elements) could be used. Also note that the membrane(s) could be formed from any suitable material(s).

Although FIG. 4 illustrates a top view of one example of a CMUT array 400 having integrated structurally-stable isolated CMUT array cells and array elements, various changes may be made to FIG. 4. For example, the array 400 could include any number of CMUT elements 402, and each CMUT element 402 could include any number of CMUT cells 404. Also, as described above, a via 410 could be formed for each CMUT cell 404, or a combination of approaches (such as vias to some CMUT elements and vias to some CMUT cells) could be used.

Figure 5:
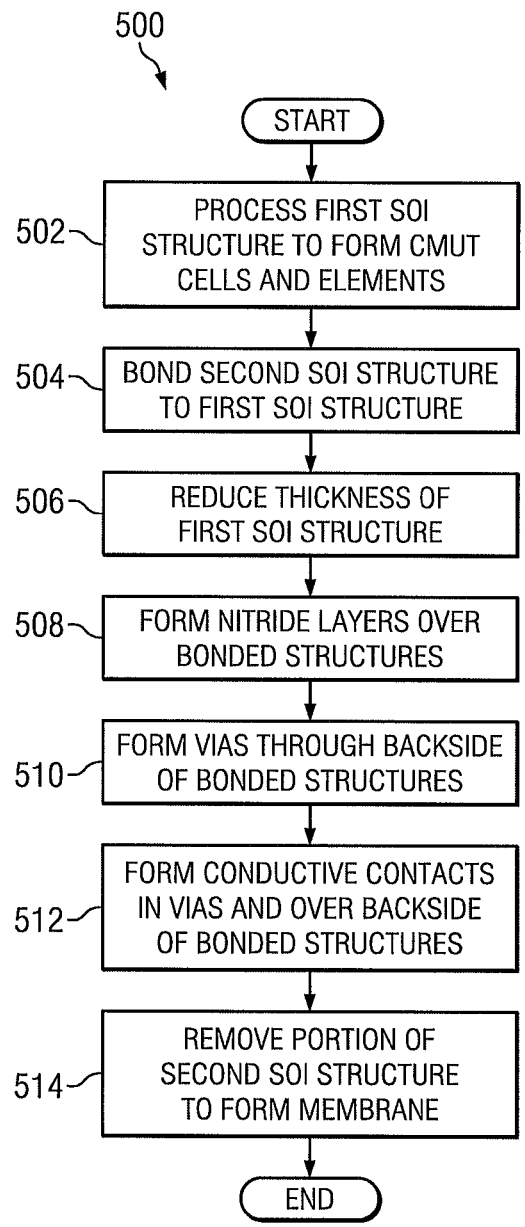
FIG. 5 illustrates an example method for forming integrated structurally-stable isolated CMUT array cells and array elements in accordance with this disclosure.

FIG. 5 illustrates an example method 500 for forming integrated structurally-stable isolated CMUT array cells and array elements in accordance with this disclosure. As shown in FIG. 5, a first SOI structure is processed to form CMUT cells and elements at step 502. This could include, for example, forming different oxide regions on the surface of an active layer 106, 206, 306 in an SOI structure to form different recessed areas. This could also include removing the oxide regions and performing any other steps to form CMUT cells and CMUT elements in the active layer 106, 206, 306. This could further include etching isolation trenches 114, 214 around the CMUT cells or elements and forming an oxide layer 116 over the CMUT cells or elements.

A second SOI structure is bonded to the first SOI structure at step 504. This could include, for example, bonding the active layer 126, 226, 326 of the second SOI structure to the oxide layer 116 on the first SOI structure. The thickness of the first SOI structure is optionally reduced at. step 506. This could include, for example, grinding or otherwise thinning the handle wafer 102, 202 of the first SOI structure.

At least one nitride layer is formed over the bonded structures at step 508. This could include, for example, forming the nitride layer 128, 328 over the top of the bonded SOI structures. This could also include forming the nitride layer 130, 230, 330 over the bottom of the bonded SOI structures.

Vias are formed through the backside of the bonded structures at step 510. This could includes, for example, etching the vias 132, 232, 332 through the handle wafer 102, 202, 302 of the first SOI structure. This could also include first forming recesses 352 in the handle wafer 302 before forming the vias 332 through the handle wafer 302 and the buried layer 304 of the first SOI structure.

Conductive contacts are formed in the vias and over the backside of the bonded structures at step 512. This could include, for example, depositing at least one conductive material into the vias 132, 232, 332 and over the backside of the bonded SOI structures. As a particular example, this could include electroplating copper or other conductive material into the vias 132, 232, 332 and over the backside of the bonded SOI structures while blocking the electroplating in certain areas using a mold mask 136. As another particular example, this could include depositing polysilicon or other conductive material into the vias 132, 232, 332 and over the backside of the bonded SOI structures and then etching the conductive material.

A portion of the second SOI structure is removed to form a membrane at step 514. This could include, for example, removing the handle wafer 122, 322 and the buried layer 124, 324 of the second SOI structure. This leaves the active area 126, 226, 326 of the second SOI structure as the membrane of the CMUT cells and elements.

Although FIG. 5 illustrates one example of a method 500 for forming integrated structurally-stable isolated CMUT array cells and array elements, various changes may be made to FIG. 5. For example, while shown as a series of steps, various steps in FIG. 5 could overlap, occur in parallel, occur in a different order, or occur multiple times. As a particular example, one nitride layer (such as layer 328) could be formed over the top of the bonded SOI structures at step 508, and another nitride layer (such as layer 330) could be formed over the bottom of the bonded SOI structures between steps 510-512. Also, various operational steps described above with respect to FIGS. 1A through 3 have been omitted for simplicity from FIG. 5.

Note that the CMUT cells are shown generically in FIGS. 1A through 4, and the formation of the CMUT cells is described generically in FIG. 5. Any suitable operations and processing steps could be used to fabricate the CMUT cells in the CMUT elements described above. For example, U.S. patent application Ser. No. 12/587,139 describes techniques for forming CMUT cells and CMUT elements over a control chip integrated into a semiconductor substrate. Such techniques could be used here to form CMUT cells and CMUT elements over a control chip integrated into an active area of an SOI structure (such as in the active areas 106, 206, 306). The electrical contacts formed through the backside of the bonded SOI structures as described above could form electrical connections to such a control chip. U.S. patent application Ser. No. 12/587,139 also provides additional details about how to form a membrane over CMUT elements or cells using an SOI structure. U.S. patent application Ser. No. 12/587,139 is hereby incorporated by reference.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method for forming a capacitive micromachined ultrasonic transducer (CMUT), the method comprising:
    forming multiple CMUT elements in a first semiconductor-on-insulator (SOI) structure, each CMUT element comprising multiple CMUT cells, the first SOI structure comprising a first handle wafer, a first buried layer, and a first active layer;
    forming a membrane over the CMUT elements; and
    forming electrical contacts through the first handle wafer and the first buried layer, the electrical contacts in electrical connection with the CMUT elements.

2. The method of claim 1, wherein forming the electrical contacts comprises:
    forming vias through the first handle wafer and the first buried layer; and
    depositing at least one conductive material into the vias.

3. The method of claim 2, wherein forming the vias comprises forming one via to each CMUT cell in each CMUT element.

4. The method of claim 2, wherein forming the vias comprises forming one via to each CMUT element.

5. The method of claim 2, wherein forming the vias comprises:
    forming multiple recesses in the first handle wafer; and
    forming the vias within the recesses.

6. The method of claim 2, wherein forming the vias comprises:
    reducing a thickness of the first handle wafer; and forming the vias through the reduced-thickness first handle wafer and the first buried layer.

7. The method of claim 2, wherein depositing the at least one conductive material comprises electroplating copper into the vias.

8. The method of claim 1, wherein forming the membrane comprises:
- bonding a second SOI structure to the first SOI structure, the second SOI structure comprising a second handle wafer, a second buried layer, and a second active layer; and
- removing the second handle wafer and the second buried layer, the membrane comprising the second active layer.

9. The method of claim 8, further comprising:
- forming an oxide layer over the CMUT cells and the CMUT elements before bonding the second SOI structure to the first SOI structure.

10. A method for forming a capacitive micromachined ultrasonic transducer (CMUT), the method comprising:
- forming multiple CMUT elements in a first semiconductor-on-insulator (SOI) structure, each CMUT element comprising multiple CMUT cells, the first SOI structure comprising a first handle wafer, a first buried layer, and a first active layer;
- forming an oxide layer over the first active layer;
- bonding a second SOI structure to the oxide layer, the second SOI structure comprising a second handle wafer, a second buried layer, and a second active layer;
- forming electrical contacts through the first handle wafer and the first buried layer, the electrical contacts in electrical connection with the CMUT elements; and
- removing the second handle wafer and the second buried layer to form a membrane over the CMUT elements.

11. The method of claim 10, wherein forming the electrical contacts comprises:
- forming vias through the first handle wafer and the first buried layer; and
- depositing at least one conductive material into the vias.

12. The method of claim 11, wherein forming the vias comprises forming one via to each CMUT cell in each CMUT element.

13. The method of claim 11, wherein forming the vias comprises forming one via to each CMUT element.

14. The method of claim 11, wherein forming the vias comprises:
- forming multiple recesses in the first handle wafer; and
- forming the vias within the recesses.

15. The method of claim 11, wherein forming the vias comprises:
- reducing a thickness of the first handle wafer; and
- forming the vias through the reduced-thickness first handle wafer and the first buried layer.

* * * * *